United States Patent [19]

Pellegrini, Jr. et al.

[11] 4,311,864

[45] Jan. 19, 1982

[54] METHOD FOR PREPARING SYNTHETIC HYDROCARBON FLUIDS

[75] Inventors: John P. Pellegrini, Jr., O'Hara Township, Allegheny County; David L. Beach; Thaddeus P. Kobylinski, both of Gibsonia, all of Pa.

[73] Assignee: Gulf Research & Development Company, Pittsburgh, Pa.

[21] Appl. No.: 168,523

[22] Filed: Jul. 14, 1980

[51] Int. Cl.$^3$ ............................................. C07C 2/02
[52] U.S. Cl. .................................................. 585/530
[58] Field of Search ......................................... 585/530

[56] References Cited

U.S. PATENT DOCUMENTS 2,421,950  6/1947  Linn ................................. 585/530

*Primary Examiner*—Curtis R. Davis
*Attorney, Agent, or Firm*—Deane E. Keith; Forrest D. Stine; Donald L. Rose

[57] ABSTRACT

A synthetic hydrocarbon fluid is prepared by oligomerizing an olefin reactant in the presence of a catalyst prepared by reacting tungsten hexafluoride and hydrogen fluoride at a moderate temperature. For example, 1-butene is oligomerized at a temperature of about 40° C. in the presence of a catalyst obtained by reacting tungsten hexafluoride and hydrogen fluoride in a four to one mol ratio. The liquid oligomer product is then hydrogenated to remove residual unsaturation.

16 Claims, No Drawings

METHOD FOR PREPARING SYNTHETIC HYDROCARBON FLUIDS

SUMMARY OF THE INVENTION

A method is provided for the oligomerization of olefins and mixtures of olefins having from three to about twelve carbon atoms, including propylene, 1-butene and 2-butene, to synthetic fluid oligomer products predominating in those fractions which are suitable, particularly after hydrogenation, for use as functional fluids. The oligomerization is carried out at a moderate temperature in the presence of a catalyst prepared by reacting tungsten hexafluoride and hydrogen fluoride.

DETAILED DESCRIPTION OF THE INVENTION

A number of processes have been proposed for the oligomerization of alpha-olefins to form synthetic fluid materials and a few have been used commercially. The olefin of choice is generally 1-decene since both the trimer and tetramer are excellent as lubricants, and the catalyst of choice is boron trifluoride since it results in the preparation of a high proportion of the trimer and tetramer of 1-decene and when used with suitable cocatalytic materials. Processes of this type are described in U.S. Pat. Nos. 3,149,178; 3,382,291; 3,763,244; 3,769,363; 3,780,128; and 3,997,621. However, no suitable prior art oligomerization process is known to us which produces high yields of oligomer fractions for use as functional fluids from propylene, 1-butene or 2-butene, or from mixtures of these olefins. We have found that boron trifluoride is essentially catalytically inactive in attempting to oligomerize these lower olefins at atmospheric pressure. On the other hand we have found that aluminum trichloride actively catalyzes these lower 1-olefins predominantly to the dimer and trimer, which oligomer product can be used in gasoline formulations. Internal olefins and in particular 2-butene are known to be difficult to oligomerize.

We have surprisingly discovered a process for oligomerizing lower olefins such as propylene and 1-butene in high yield to those liquid oligomer fractions which are suitable for use as functional fluids. More surprisingly our novel process also oligomerizes 2-butene to oligomer fractions suitable for use as functional fluids in high yield. And most surprisingly we have discovered that these oligomerization reactions can be carried out at atmospheric pressure. These lower olefins can be individually oligomerized or they can be co-oligomerized by our process. Our process can be used to oligomerize or co-oligomerize higher 1-olefins either separately or jointly with these lower olefins to produce useful synthetic fluids. Therefore, we find that our novel process relates to the oligomerization or co-oligomerization of one or more olefins selected from 2-butene and 1-olefins having from three to about twelve carbon atoms as defined by the formula $CH_2=CH-R$, wherein R is alkyl having from one to about ten carbon atoms.

The catalyst used in our process is the reaction product of tungsten hexafluoride and hydrogen fluoride. It is prepared by reacting tungsten hexafluoride and hydrogen fluoride, either externally or in situ, using a critical ratio of the two components. We have found that oligomerization does not occur when hydrogen fluoride is excluded both from the catalyst and the reaction system. Since this catalyst is soluble in the hydrocarbon reaction medium, a homogeneous reaction system is formed.

Superior results can be obtained in converting the olefin to oligomer product and in obtaining selectivity to the desired oligomer fractions when the mol ratio of tungsten hexafluoride to hydrogen fluoride is controlled within specified limits. Thus, we find that for suitable results the catalyst should be prepared by using at least about 0.05 mol of hydrogen fluoride per mol of tungsten hexafluoride up to a maximum of about one mol of hydrogen fluoride per mol of tungsten hexafluoride. However, we can broadly define the relative amounts of tungsten hexafluoride and hydrogen fluoride that can be used as being catalytically effective ratio of these two catalyst components. We prefer a mol ratio of tungsten hexafluoride to hydrogen fluoride of between about 3:1 and about 10:1 and most prefer a ratio of about 4:1 to about 5:1. Sufficient catalyst is utilized in the oligomerization reaction to accomplish the oligomerization of the desired quantity of olefin. A large excess of the catalyst can be used, but this would, in general, not be desirable unless the tungsten hexafluoride and the hydrogen fluoride are eventually recovered, such as by a vaporization procedure.

The oligomerization is desirably carried out in the liquid phase in a suitable inert liquid solvent such as a paraffinic hydrocarbon or a halogenated paraffinic hydrocarbon. The amount of the inert solvent that can conveniently be used is from about zero percent up to about 75 weight percent of the total oligomerization reaction system. However, we prefer that the solvent comprise between about 5 and about 50 weight percent of the total reaction system. Suitable solvents include the liquid alkanes and cycloalkanes having between about five and about 60 carbon atoms, such as pentane, hexane, heptane, octane, cyclopentane, cyclohexane, or, alternatively, the unhydrogenated or hydrogenated oligomer reaction product or fraction thereof, and the like. Also useful as solvent are the halogenated alkanes having from one to about 20 carbon atoms, such as carbon tetrachloride, chloroform, ethylene dichloride, and the like. Aromatic compounds such as benzene are not inert since they are alkylated by the olefin reactant. Certain oxygen-containing organic compounds such as methanol, ethanol, acetone, dioxane and triglyme are not useful because they have been found to deactivate the catalyst. It is desirable that the boiling point of the solvent at 760 mm Hg be between 30° and about 500° C. When the catalyst is made up as a solution in the solvent, it is preferred that the catalyst comprise between about 10 and about 50 weight percent of the solution, but catalyst solutions outside this range are also useful.

A solvent is desirably selected having a boiling point which is well above the reaction temperature so that the liquid state can be easily maintained in the reactor. At the same time the boiling point is also desirably selected which is sufficiently different from any reactant or oligomer product to permit simple distillative separation of the various constituents in the reaction product. In general, an inert solvent is used in the reaction, although it is also possible to use an excess of the olefin as a solvent, such as by carrying out the oligomerization as a simple batch reaction. But this procedure is generally avoided since using excess olefin as the reaction medium makes it more difficult both to carry out the reaction and to control the reaction temperature. The solvent not only functions as a medium for dissolving both the reactants and the catalyst but it also desirably serves as a heat sink to help control the temperature of the exothermic oligomerization reaction.

The reaction can suitably be carried out at a temperature between about 2° C. and about 100° C., but it is preferably carried out at a temperature between about 15° C. and about 70° C. Since tungsten hexafluoride solidifies at about 2° C., this temperature is selected as a convenient minimum operating temperature. The upper limit of about 100° C. is selected because the catalyst begins to decompose above this temperature. The pressure in the reactor is not critical. A particular advantage of the present process is that it can be carried out at atmospheric pressure, in fact, the most preferred pressure range is about one to about five atmospheres. However, the reaction can be carried out at subatmospheric pressures as well as at elevated pressures including pressures up to about 1,000 psia and higher.

In carrying out the reaction we prefer to make the catalyst in situ by separately adding suitable quantities of the tungsten hexafluoride and the hydrogen fluoride to the reaction solvent, however, it can also be prepared ex situ and then introduced into the reactor. The olefin is then added incrementally such as by metering it into the reactor at a rate to maintain the desired temperature for the exothermic reaction. Supplemental heating or cooling of the reaction liquid may also be desirable. We have also found as a variant of this procedure that a minor portion of the olefin reactant can first be added to the reaction solvent followed by the tungsten hexafluoride and then the hydrogen fluoride. Perceptible oligomerization does not take place until the hydrogen fluoride is added. The reaction is then completed by metering in the remaining portion of the olefin to the reaction liquid. The greater the concentration of the catalyst in the solution the greater the reaction rate. Therefore, although the oligomerization will take place, albeit slowly, in extremely dilute catalyst solutions, it is preferred that sufficient catalyst be used to provide a suitable reaction rate at the reaction conditions being utilized, taking notice that the catalyst is diluted as the olefin is metered into the reaction solution.

Since tungsten hexafluoride and the reaction product of tungsten hexafluoride and hydrogen fluoride are soluble in paraffinic hydrocarbon solvents, they are most conveniently utilized as a solution in the same solvent that will be used as the reaction medium so that they can be conveniently handled and added to the reaction zone in appropriate amounts as required. However, gaseous tungsten hexafluoride and gaseous hydrogen fluoride are also suitable and can be dissolved in situ by injecting them directly into the reactor liquid.

The expressions synthetic fluids, synthetic oils and functional fluids are used herein with reference to those synthetic hydrocarbon fractions which have between about 20 and about 60 carbon atoms per molecule, therefore, the term oligomer is used herein with reference to products having up to about 60 carbon atoms. This carbon number range corresponds to a molecular weight range of between about 280 and about 840. Useful functional fluids which may be obtained by our process include, for example, but are not necessarily restricted to lubricating oils, hydraulic fluids, transmission fluids, transformer fluids, vehicles for pesticides and herbicides, and the like. The preferred lubricating oil range from which automobile engine lubricating oils are desirably prepared are those hydrocarbon fractions which have between about 28 and 44 carbon atoms per molecule.

The carbon number or molecular weight distribution of the product can be controlled to some degree by controlling the reaction temperature and the time of reaction. The higher the temperature and the shorter the reaction time the lower the average molecular weight of the oligomer product. Therefore, if a lower average product molecular weight is desired, the oligomerization is carried out at a higher temperature within the specified range. The total reaction time can also be reduced but this may also reduce the amount of the olefin that is reacted. The lower oligomer fractions, such as those containing up to about 19 carbon atoms or higher, as desired, can be separated from the reaction product and recycled to the reactor for reaction with the feed olefin to build up the molecular weight to a desired level. On the other hand, if there is no current use for an oligomer fraction having a high molecular weight, such as the fraction having more than 44 carbon atoms per molecule, the high molecular weight product fraction may present a process loss. Process efficiency can therefore be effected by operating at conditions for a somewhat lower average molecular weight than is actually desired and recycling the light ends to convert them to a useful product.

Separation of the oligomer product by fractional distillation can be conveniently accomplished up to about 36 to about 44 carbon atoms with separation by distillation becoming increasingly more difficult the higher the carbon number. Therefore, the still bottoms containing more than about 36 to 44 carbon atoms is generally recovered as one product. This high-molecular weight still bottoms product can either be utilized as a functional fluid, such as a lubricant in specific applications requiring a high viscosity lubricant, or it can be diluted with lower viscosity material to produce a product of moderately high viscosity. When produced in excess, the still bottoms can be cracked into lower molecular weight components or burned as a fuel. This still bottoms product can contain a minor amount of oligomer fractions having more than 60 carbon atoms which will vary in amount depending on the conditions under which the oligomerization reaction is conducted. The oligomer product is generally hydrogenated prior to use to remove olefinic unsaturation and thereby stabilize the product. Conventional hydrogenation procedures and catalyst can be used such as Raney nickel, supported platinum or palladium, and the like at a suitable elevated temperature and pressure.

DESCRIPTION OF PREFERRED EMBODIMENTS

Fuel grade n-heptane which had been dried in a molecular sieve and commercial grade dry olefin were used in the following experiments. The reactors were three-neck round bottom flasks of various sizes equipped with rubber septum, Teflon-coated magnetic stirring bar, thermocouple well, and reflux condenser containing a solid carbon dioxide cold-finger at the upper end. Moderation and control of the reaction temperature were obtained by placing the reactor in a water bath at about 20° C.

EXAMPLE 1

This experiment demonstrates that tungsten hexafluoride is inactive for the oligomerization reaction of 1-butene. A 100 ml portion of n-heptane was charged into a 500 ml flask. About 1.5 g of liquid tungsten hexafluoride was injected into the reactor from a cylinder and 81 g of 1-butene was bubbled into the reactor. The color of the solution was pale yellow. There was no temperature rise over a period of 215 minutes and no reaction was observed. There was no change in the color of the solution during this period of time.

EXAMPLE 2

Example 1 was repeated using hydrogen fluoride instead of tungsten hexafluoride and no oligomerization of 1-butene resulted. Fifty milliliters of n-heptane was charged to a 125 ml flask at 18° C. About 0.01 g of gaseous hydrogen fluoride was injected into the n-heptane over a period of ten seconds. A 14 g quantity of 1-butene was charged into the solution. There was no evidence of any reaction over an 11 minute period of time. The solution was clear and colorless both at the beginning and at the end of the observation period.

EXAMPLE 3

This example demonstrates that the reaction product of tungsten hexafluoride and hydrogen fluoride is an active catalyst for the oligomerization of 1-butene. A 50 g amount of n-heptane was charged to a 125 ml flask at 18° C. About 10 g of 1-butene were added to saturation. The heat of solution caused the temperature to rise to about 32° C. After the temperature had dropped back to 18° C., 10 ml of a pale yellow solution containing 2.24 g of tungsten hexafluoride in n-heptane was charged to the reactor. After standing for six minutes with no reaction, about 0.1 g of hydrogen fluoride gas was injected into the liquid over a period of five seconds. Reaction was instantaneous as the color of the reaction liquid started turning brown and eventually reaching dark brown. The temperature rose to a maximum of about 26° C. after 22 minutes. An additional 36 g of 1-butene was added to the reaction liquid over a 75 minute period of time.

At the completion of the reaction the catalyst was deactivated by agitation with an excess of water to form $WO_3 \cdot 2H_2O$. The organic layer was separated and washed with aqueous sodium hydroxide to neutralize the hydrogen fluoride and then washed with water until neutral. The organic product was dried over anhydrous sodium sulfate and the n-heptane was removed by heating under vacuum to yield 40 g of a light yellow, clear oligomer oil. This represented a conversion of 87 percent. Gas chromatographic analysis of the oligomer product disclosed one percent $C_{12}$ oligomer, 4 percent $C_{16}$ oligomer, 6 percent $C_{20}$ oligomer, 7 percent $C_{24}$ oligomer, 10 percent $C_{28}$ oligomer, 11 percent $C_{32}$ oligomer, 12 percent $C_{36}$ oligomer and 49 percent higher than $C_{36}$. No dimer was identified.

It is to be understood that the above disclosure is by way of specific example and that numerous modifications and variations are available to those of ordinary skill in the art without departing from the true spirit and scope of the invention.

We claim:

1. A method for preparing a synthetic hydrocarbon functional fluid in a homogeneous reaction system which comprises contacting an olefin reactant selected from 2-butene, an olefin having the formula $CH_2=CH-R$ wherein R is alkyl having from one to about ten carbon atoms, and mixtures thereof at a temperature between about 2° C. and about 100° C. with a catalytic amount of the reaction product of tungsten hexafluoride and hydrogen fluoride wherein tungsten hexafluoride and hydrogen fluoride in a mol ratio of between about 1:1 and about 20:1 are reacted to form the catalyst, and recovering an oligomer product predominating in synthetic hydrocarbon fractions having between about 20 and about 60 carbon atoms.

2. A method for preparing a synthetic hydrocarbon fluid in accordance with claim 1 in which the olefin reactant comprises 1-butene.

3. A method for preparing a synthetic hydrocarbon fluid in accordance with claim 1 in which the olefin reaction comprises 2-butene.

4. A method for preparing a synthetic hydrocarbon fluid in accordance with claim 1 in which the olefin reactant comprises a mixture of 1-butene and 2-butene.

5. A method for preparing a synthetic hydrocarbon fluid in accordance with claim 1 in which the olefin reactant comprises propylene.

6. A method for preparing a synthetic hydrocarbon fluid in accordance with claims 2, 3, 4 or 5 in which the olefin reactant comprises said lower olefin and from about 20 to about 80 mol percent of one or more olefins wherein R is alkyl having from about four to about 10 carbon atoms.

7. A method for preparing a synthetic hydrocarbon fluid in accordance with claim 1 in which tungsten hexafluoride and hydrogen fluoride are reacted in a mol ratio of between about 3:1 and about 10:1.

8. A method for preparing a synthetic hydrocarbon fluid in accordance with claim 1 in which the reaction mixture is between about 15° C. and about 70° C.

9. A method for preparing a synthetic hydrocarbon fluid in accordance with claim 1 in which the olefin reactant additionally comprises a recycle light end having at least 12 carbon atoms and no greater than about 24 carbon atoms.

10. A method for preparing a synthetic hydrocarbon fluid in accordance with claim 1 in which tungsten hexafluoride and hydrogen fluoride are reacted in a mol ratio of between about 4:1 and about 5:1.

11. A method for preparing a synthetic hydrocarbon fluid in accordance with claim 1 in which the oligomer product predominates in fractions having between about 28 and about 44 carbon atoms.

12. A method for preparing a synthetic hydrocarbon fluid in accordance with claim 1 in which the oligomer product predominates in fractions having between about 20 and about 32 carbon atoms.

13. A method for preparing a synthetic hydrocarbon fluid in accordance with claim 1 in which the oligomer product is hydrogenated.

14. A method for preparing a synthetic hydrocarbon fluid in accordance with claim 1 in which the reaction mixture comprises an inert liquid organic solvent.

15. A method for preparing a synthetic hydrocarbon fluid in accordance with claim 14 in which said solvent is selected from alkanes and cycloalkanes having from about five to about 60 carbon atoms and halogenated alkanes having from one to about 20 carbon atoms.

16. A method for preparing a synthetic hydrocarbon fluid in accordance with claim 14 in which said solvent comprises from about five to about 50 weight percent of said reaction mixture.

* * * * *